United States Patent [19]

Beguin et al.

[11] 4,235,736
[45] Nov. 25, 1980

[54] DIPHENYLIC ESTERS EXHIBITING MESOMORPHIC PHASES

[75] Inventors: Alain Beguin; Jean-Claude Dubois; Annie Zann, all of Paris, France

[73] Assignee: Thomson-CSF, Paris, France

[21] Appl. No.: 29,536

[22] Filed: Apr. 12, 1979

Related U.S. Application Data

[63] Continuation-in-part of Ser. No. 875,931, Feb. 7, 1978, abandoned.

[30] Foreign Application Priority Data

Feb. 11, 1977 [FR] France .................. 77 03916
Jan. 24, 1978 [FR] France .................. 78 01880

[51] Int. Cl.³ .................. C09K 3/34; G02F 1/13; C07C 121/60; C07C 69/62
[52] U.S. Cl. .................. 252/299; 252/408; 260/465 D; 350/350 R; 560/62; 560/65; 560/108
[58] Field of Search .................. 252/299, 408; 350/350, 350/346; 260/465 D; 560/62, 65, 108

[56] References Cited

U.S. PATENT DOCUMENTS

| | | |
|---|---|---|
| 3,915,883 | 10/1975 | Van Meter et al. .................. 252/299 |
| 3,951,846 | 4/1976 | Gavrilovic .................. 252/299 |
| 3,953,491 | 4/1976 | Steinstrasser et al. .................. 252/299 |
| 4,001,137 | 1/1977 | Steinstrasser .................. 252/299 |
| 4,009,934 | 3/1977 | Goodwin et al. .................. 252/299 |
| 4,029,594 | 6/1977 | Gavrilovic et al. .................. 252/299 |
| 4,065,489 | 12/1977 | Steinstrasser et al. .................. 252/299 |
| 4,073,742 | 2/1978 | Erdmann et al. .................. 252/299 |
| 4,110,243 | 8/1978 | Abert-Mellah et al. .................. 252/299 |
| 4,138,359 | 2/1979 | Mizukuchi .................. 252/299 |
| 4,173,545 | 11/1979 | Beguin et al. .................. 252/299 |

FOREIGN PATENT DOCUMENTS 2715519 10/1977 Fed. Rep. of Germany .......... 252/299
2836086 3/1979 Fed. Rep. of Germany .......... 252/299

OTHER PUBLICATIONS

Gray, G. W., et al., Mol. Cryst. Liq. Cryst., vol. 37, pp. 157-188 (1976).
Dubois, J. C., et al., Mol. Cryst. Liq. Cryst., vol. 42, pp. 139-152 (Aug. 1977).
Gray, G. W., Molecular Structure and the Properties of Liquid Crystals, Academic Press, N. Y., p. 149 (1962).
Demus, et al., Flussige Kristalle in Tabellen, pp. 188-190 and 201 (1974).

*Primary Examiner*—Teddy S. Gron
*Attorney, Agent, or Firm*—Cushman, Darby & Cushman

[57] ABSTRACT

A family of diphenylic esters are disclosed, which, within certain temperature ranges exhibit mesomorphic phases, either smectic or nematic, having the general formula:

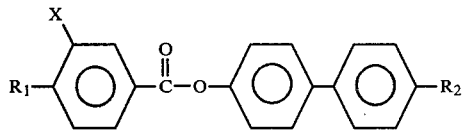

where
$R_1$ is $C_nH_{2n+1}O$ or $C_nH_{2n+1}$ in which n is an integer of from 1 to 10,
$R_2$ is $C_mH_{2m+1}$ in which m is an integer of from 1 to 10, and
X is Br or CN.

12 Claims, No Drawings

DIPHENYLIC ESTERS EXHIBITING MESOMORPHIC PHASES

CROSS-REFERENCE TO RELATED APPLICATIONS

This is a continuation-in-part of our copending application Ser. No. 875,931, filed Feb. 7, 1978, now abandoned.

DESCRIPTION OF THE INVENTION

The present invention relates to a series of diphenylic esters forming a family of liquid crystal compounds which differ from one another simply in terms of the organic groups $C_nH_{2n+1}$ or $C_nH_{2n+1}O$ and in terms of a bromine or cyano group. These compounds, taken singly or in mixtures with one another, can exhibit mesomorphic phases, and specifically either a nematic phase, or one or more smectic phases, or a nematic phase and one or more smectic phases.

These liquid crystals correspond to the following general formula:

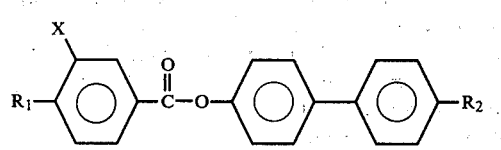

in which
$R_1 = C_nH_{2n+1}O$ or $C_nH_{2n+1}$, where n is an integer of from 1 to 10;
$R_2 = C_mH_{2m+1}$ where m is an integer of from 1 to 10;
X = Br or CN. Preferably $R_1$ is $C_6H_{13}$ or $C_7H_{15}$ or $C_8H_{17}O$ and $R_2$ is $C_6H_{13}$ or $C_5H_{11}$.

Various compounds within the family are designated as follows:
p-alkyldiphenyl-alkoxy-4bromo-3 benzoate, when $R_1$ is an alkoxy group and X is bromine;
p-alkyldiphenyl-alkoxy-4 cyano-3 benzoate, when $R_1$ is an alkoxy group and X is a CN group;
p-alkyldiphenyl-alkyl-4 bromo-3 benzoate, when $R_1$ is an alkyl group and X is bromine; and
p-alkyldiphenyl-alkyl-4 cyano-3 benzoate, when $R_1$ is an alkyl group and X is a CN group.

$R_1$ and $R_2$ are preferably straight-chained alkyl groups within the above-stated carbon atom range.

Compounds of the invention are prepared according to the following general outline of the method of preparation in accordance with the present invention, following which particular examples of preferred synthesis routes will be described.

According to this general outline, hydroxy-alkyl-diphenyl is first synthethized and then, depending upon the particular case alkoxy-bromo-benzoic acid or alkyl-bromo-benzoic acid, under the conditions described below, in order thus to obtain the desired alkoxy or alkyl-bromobenzoate.

To obtain compounds which contain CN, the bromine in the bromated compounds is substituted in the manner described hereafter.

In a preferred method the following intermediate compounds are synthesized:
(1) 4-hydroxy-4'-alkyl biphenyl;
(2) 4-alkoxy-3-bromobenzoyl chloride.

The bromine compound is synthesized from the two intermediate compounds, the cyano compound then being synthesized from the bromine compound.

The synthesis of the first intermediate compound is carried out in accordance with the following scheme:
(a) Synthesis of 4-alkanoyloxy-4'-alkanoyl biphenyl

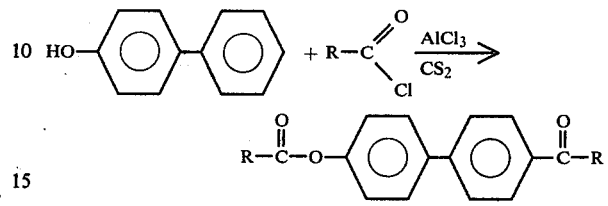

where R is an alkyl radical.
(b) Synthesis of 4-hydroxy-4'-alkyl biphenyl

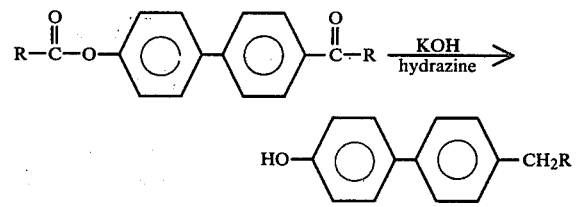

The group $-CH_2-R$ represents the group $R_2$ in the general formula. This process is preferred as it provides a much higher yield of the desired products.

Another method of synthesizing is as follows, where R is an alkyl group:
(1) Friedel and Kraft Reaction:

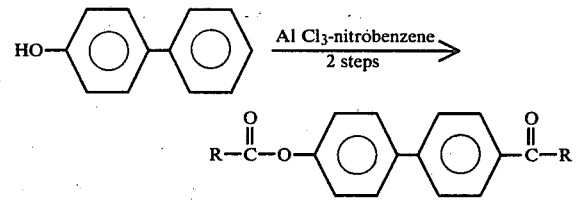

(2) Wolff-Kishner Reaction:

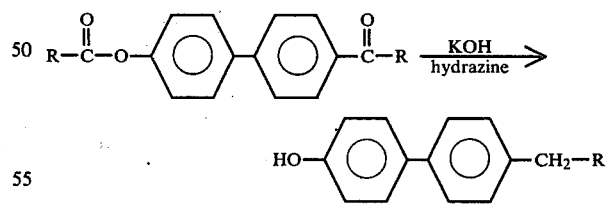

The $-CH_2-R$ group represents the group $R_2$ in the general formula.
(c) Synthesis of 4-alkoxy-3-bromobenzoic acid

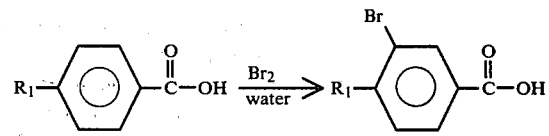

where $R_1 = C_nH_{2n+1}O$ (d) Synthesis of 4-alkyl-3-bromobenzoic acid

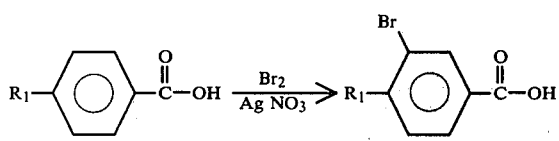

where $R_1 = C_nH_{2n+1}$.

(e) Synthesis of 4-alkoxy (or alkyl)-3-bromobenzoyl chloride

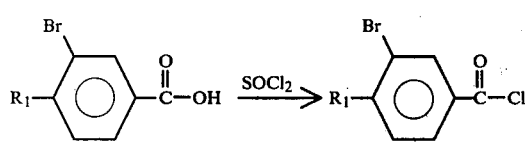

where $R_1$ is either an alkoxy or an alkyl radical.

(f) Synthesis of p-alkyl-diphenyl-4-alkoxy (or alkyl)3-bromo benzoate

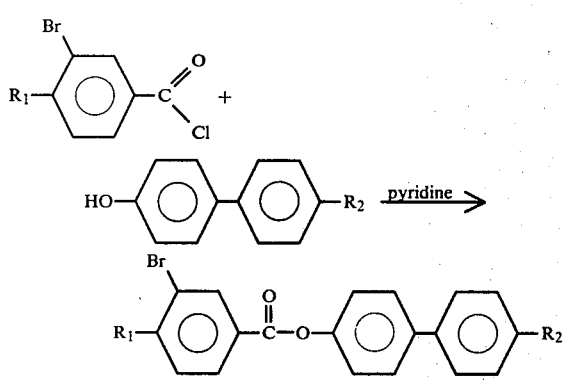

where $R_2$ is an alkyl group.

The cyano compound is then synthesized in accordance with the following reaction scheme:

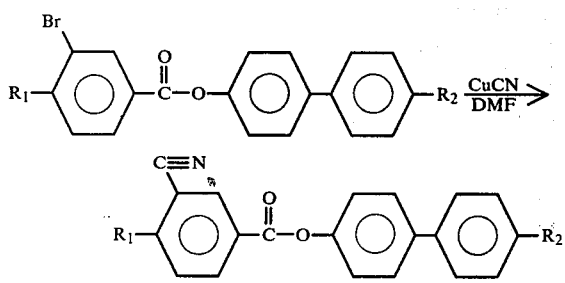

where DMF stands for dimethyl formamide (solvent) and $R_1$ and $R_2$ indicate the same groups as before.

The following are given as examples of the invention wherein diphenylic esters of the general formula are prepared in which the $R_1$ group is octyloxy and the $R_2$ group is pentyl.

EXAMPLE I

Synthesis of 3-bromo-4-octyloxy benzoic acid

The starting point is p-octyloxy-benzoic acid.

Into 180 ml of deionized water there are placed in suspension 37.5 g (0.15 moles) of p-oxtyloxy-benzoic acid. The temperature of the reaction medium is raised to between 50° and 55° C. and at this temperature 8.7 ml (0.17 moles) of bromine are added stepwise over a period of 7 hours, 30 minutes. The product is then filtered, rinsed in deionized water and recrystallized in ethanol; 37.9 g of pure product having a melting point of 110° C., are then obtained.

EXAMPLE II

Synthesis of p-pentyl-biphenyl-3-bromo-4-octyloxy benzoate 2.4 g (0.01 moles) of 4-hydroxy-4'-pentyl biphenyl are dissolved in 20 ml of pyridine. 3.475 g (0.01 moles) of 3-bromine-4-octyloxy benzoyl chloride, are added. The solution is agitated at ambient temperature for a period of three days. The solution is then poured into a mixture of 70 g of ice and 8 ml of concentrated sulfuric acid. The solution is stirred followed by extraction using benzene. The result is 5.8 g of crude product which is purified by chromatography on a silica column, followed by re-crystallization with ethanol. 3.7 g of the desired pure product are obtained.

EXAMPLE III

Synthesis of p-pentyl biphenyl-3-cyano-4-octyloxy benzoate 2.75 g ($5.10^{-3}$ moles) of p-pentyl biphenyl-3-bromo-4-octyloxy benzoate and 0.6 g ($6.7.10^{-3}$ moles) of cuprous cyanide are introduced into 10 ml of dimethyl formamide. After system had been heated under reflux for 6 hours, it is cooled and poured into a mixture of 60 ml of deionized water and 5.5 ml of ethylene diamine. The solution is stirred and then extracted with ether. 2.3 g of crude product are obtained and then purified chromatographically on a column of silica, followed by recrystallization in ethanol. 1.8 g of pure product are obtained.

EXAMPLE IV

Synthesis of 4-hexanoypoxy-4'-hexanoyl biphenyl according to reaction (a), above 34 g (0.2 mole) of 4-hydroxy biphenyl are added to 100 ml of carbon disulphide. The solution is stirred and 53.5 g (0.4 mole) of aluminium chloride are added over a period of 5 minutes. After heating to reflux temperature, 54 g (0.4 mole) of hexanoyl chloride are added over a period of 1 hour. Heating under reflux is then continued for 3 hours.

The solution is then cooled and poured into a mixture of 200 g of ice and 100 ml of concentrated hydrochloric acid. It is extracted with benzene.

The benzene extracts are then wasted with deionized water and dried over magnesium sulphate.

The solvent is distilled. 73.6 g of mixture are collected and recrystallized from 200 ml of a solution of benzene and ethanol (50/50).

52.5 g of pure product are obtained, corresponding to a yield of 72%.

EXAMPLE V

Synthesis of 4-hydroxy-4'-hexyl biphenyl, according to reaction (b), above 450 g (8 moles) of potassium hydroxide and 45.7 g (1.25 moles) of 4-hexanoyloxy-4'-hexanoyl biphenyl are added to a solution of 1.2 liters of diethylene glycol and 282 g (9 moles) hydrazine hydrate. The solution is heated under reflux for 2 hours, after which the water and excess hydrazine are distilled up to a "mass" temperature of 228° C.

The solution is left to cool to 100° C. and then poured into 6 liters of deionized water. After stirring for 1 hour, the solution obtained is acidified to pH 1-2 with concentrated hydrochloric acid. The product precipitates and is extracted with ether.

The extract obtained is washed with deionized water and then dried over magnesium sulfate. The ether is distilled and the remaining product is recrystallized from 600 ml of hexane.

28.9 g of pure product are obtained, corresponding to a yield of 91%.

EXAMPLE VI

Synthesis of p-hexyl biphenyl-3-bromo-4-heptyl benzoate 2.54 g (0.01 mole) of 4-hydroxy-4'-hexyl biphenyl are dissolved in 20 ml of pyridine. 3.175 g (0.01 mole) of 3-bromo-4-heptyl benzoyl chloride are added, followed by stirring at ambient temperature for 3 days. The solution is poured into a mixture of 70 g of ice and 8 ml of concentrated sulfuric acid. After stirring, the reaction mixture is extracted with benzene. 5.7 g of crude product are obtained, being purified by chromatography on a column of silica, followed by recrystallization from ethanol. 3.5 g of pure product are obtained, corresponding to a yield of 65%.

EXAMPLE VII

Synthesis of p-hexyl biphenyl-3-cyano-4-heptyl benzoate 2.65 g ($5.10^{-3}$ moles) of p-hexyl biphenyl-3-bromo-4-heptyl benzoate and 0.6 g ($6.7 \times 10^{-3}$ moles) of cuprous cyanide are introduced into 10 ml of dimethyl formamide. After the solution has been heated under reflux for 7.5 hours, it is cooled and poured into a mixture of 60 ml of deionized water and 5.5 ml of ethylene diamine. After stirring, the solution is extracted with ether. 2.2 g of crude product are obtained, being purified by chromatography on a column of silica, followed by recrystallization from ethanol. 1.6 g of pure product are obtained, corresponding to a yield of 66%.

PROPERTIES OF THE COMPOUNDS AND MIXTURES

To facilitate explanation, the following symbols are used hereinafter:

K = crystalline phase
$S_A$ = smectic phase A
$S_C$ = smectic phase C
N = nematic phase
I = isotropic liquid phase
$\epsilon_{par}$ = "parallel" dielectric constant at 22° C.
$\epsilon_{perp}$ = "perpendicular" dielectric constant at 22° C.
$\epsilon_a$ = dielectric anisotropy or in other words $\epsilon_{par} - \epsilon_{perp}$ The numbers indicated between the phase symbols in Table I denote the transition temperature in °C.

TABLE 1

| Reference | Formula of Compound (or definition of mixture) | Mesomorphic Range |
|---|---|---|
| A | 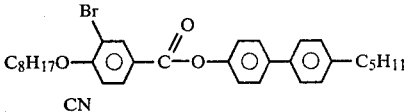 | K 111 $S_c$ 112 N 148 I |
| B | 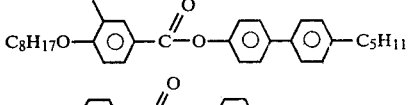 | K 99 $S_c$ 158 $S_A$ 159 I |
| C* | 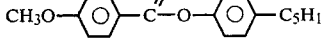 | K 29 N 43 I |
| D | 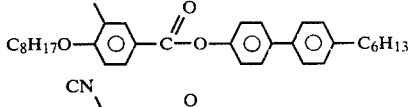 | K 116 $S_c$ 120 N 144 I |
| E | 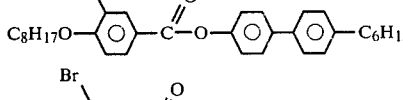 | K 91.5 $S_c$ 136 $S_A$ 158 I |
| F | 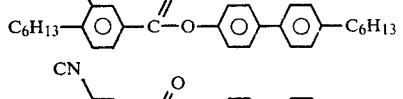 | K 46 $S_c$ 86 N 109 I |
| G | 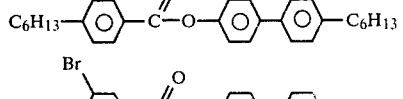 | K 61 $S_A$ 112 I |
| H | 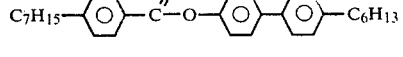 | K 56 $S_c$ 84.5 N 109 I |

TABLE 1-continued

| Reference | Formula of Compound (or definition of mixture) | Mesomorphic Range |
|---|---|---|
| I | (structure with CN, $C_7H_{15}$, $C_6H_{13}$) | K 69 $S_A$ 117.5 I |
| J | Mixture containing 0.1 mole of compound B and 0.9 mole of compound C | K 20 N 60 I |
| K | Mixture containing 0.1 mole of compound G and 0.9 mole of compound C | K 25 N 40 I |

*not according to the present invention.

TABLE 2

| Analyzed Product | $\epsilon_{par}$ | $\epsilon_{perp}$ | $\epsilon_a$ |
|---|---|---|---|
| Nematic liquid crystal alone (Compound C) | 5.7 | 5.6 | +0.1 |
| Mixture J | 5.6 | 6.5 | −0.9 |
| Mixture K | 5.5 | 6.0 | −0.5 |

The compounds according to the invention may be used inter alia in the following electrooptical devices:

display systems based on the dynamic diffusion of light which require a wide temperature range and a negative dielectric anisotropy, these two properties being exhibited in particular by mixtures of nematic liquid crystals with compounds according to the invention;

electrooptical devices utilizing the property whereby the negative dielectric anisotropy is more or less pronounced according to whether the frequency of the electrical field prevailing in the liquid crystal is of the order of a few thousand or a few hundred thousand hertz;

display systems of the so-called "field-effect memory" type or thermo-optical memory display systems in the case of compounds according to the invention having a smectic phase (compounds E, G and I of Table 1).

What is claimed is:

1. A liquid crystal corresponding to the formula:

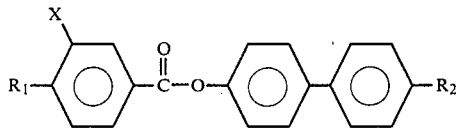

wherein
R$_1$ is C$_n$H$_{2n+1}$O or C$_n$H$_{2n+1}$,
where
n is an integer of from 1 to 10;
R$_2$ is C$_m$H$_{2m+1}$,
where
m is an integer of from 1 to 10; and
X is Br or CN.

2. The liquid crystal as claimed in claim 1 having the formula:

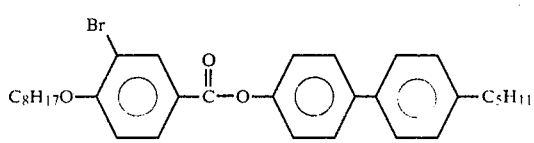

3. The liquid crystal as claimed in claim 1 having the formula:

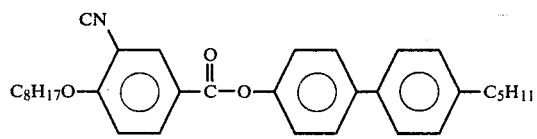

4. The liquid crystal as claimed in claim 1 having the formula:

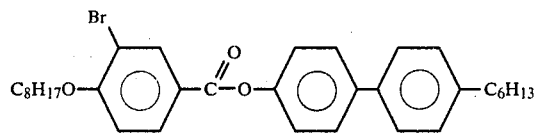

5. The liquid crystal as claimed in claim 1 having the formula:

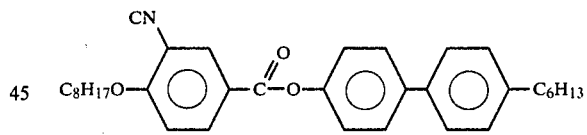

6. The liquid crystal as claimed in claim 1 having the formula:

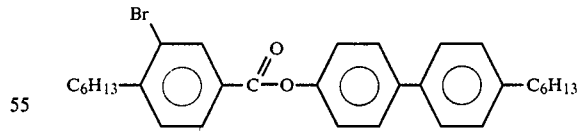

7. The liquid crystal as claimed in claim 1 having the formula:

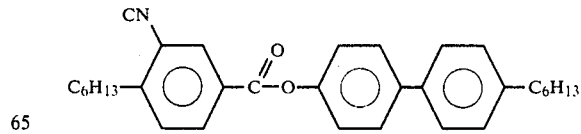

8. The liquid crystal as claimed in claim 1 having the formula:

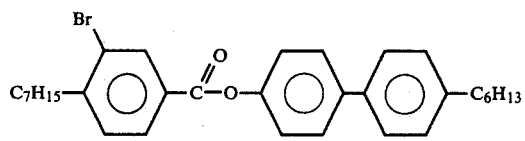

9. The liquid crystal as claimed in claim 1 having the formula:

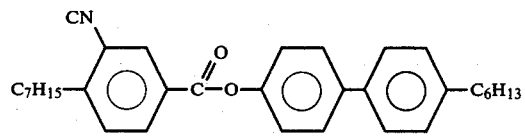

10. A mixture of liquid crystals suitable for use in a liquid crystal cell consisting of:

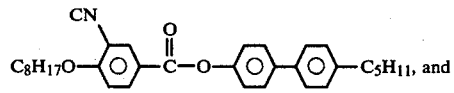 A

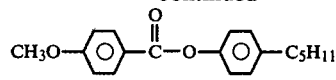 B the molar ratio of A to B being 0.1:0.9.

11. A liquid crystal corresponding to the formula:

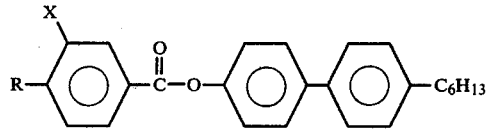

in which:
R=C$_6$H$_{13}$ or C$_7$H$_{15}$ or C$_8$H$_{17}$O; and
X=Br or CN.

12. A mixture of liquid crystals suitable for use in a liquid crystal cell consisting of:

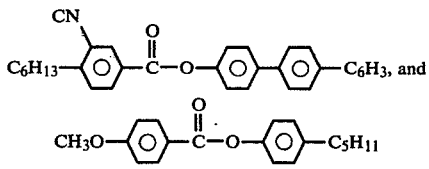

the molar ratio of A to B being about 0.1:0.9.

* * * * *